United States Patent [19]

Sauers

[11] 4,217,312

[45] Aug. 12, 1980

[54] 1-ALKYL-2,2-DICHLORO-2(PHOSPHINYL-)ACETATES

[75] Inventor: Richard F. Sauers, Hockessin, Del.

[73] Assignee: E. I. Du Pont de Nemours and Company, Wilmington, Del.

[21] Appl. No.: 930,600

[22] Filed: Aug. 1, 1978

Related U.S. Application Data

[63] Continuation-in-part of Ser. No. 914,757, Jun. 14, 1978, abandoned, which is a continuation-in-part of Ser. No. 828,213, Aug. 26, 1977, abandoned.

[51] Int. Cl.² .............................. A01N 9/36; C07F 9/32
[52] U.S. Cl. ............................................ 260/941; 71/86; 71/87; 260/326.2; 260/986; 544/157; 544/337; 546/21; 560/105; 560/226; 549/6
[58] Field of Search ............................. 260/941; 71/86; 560/105, 226

[56] References Cited

U.S. PATENT DOCUMENTS

3,662,039  5/1972  Nicholson ..................... 260/941 X

FOREIGN PATENT DOCUMENTS

10747  12/1955  Fed. Rep. of Germany ........... 260/941
331847  9/1958  Switzerland ............................. 260/941

OTHER PUBLICATIONS

Lichtenthaler, "Chemical Reviews", vol. 61, (1961) pp. 607-648.

*Primary Examiner*—Anton H. Sutto

[57] ABSTRACT

This invention relates to phosphorus containing compounds which are useful as herbicides.

Additionally, they demonstrate tolerance towards desired crops, e.g., cotton, soybeans and sugarbeets.

9 Claims, No Drawings

1-ALKYL-2,2-DICHLORO-2(PHOSPHINYL)ACETATES

RELATED APPLICATIONS

This application is a continuation-in-part of my co-pending application U.S. Ser. No. 914,757 filed June 14, 1978 which in turn is a continuation-in-part of my application U.S. Ser. No. 828,213 filed Aug. 26, 1977, both now abandoned.

BACKGROUND OF THE INVENTION

German Offenlegungsschrift F107471Vb/120 describes the preparation of compounds of Formula A by Equation 1. These compounds are disclosed to be insecticides.

EQUATION 1

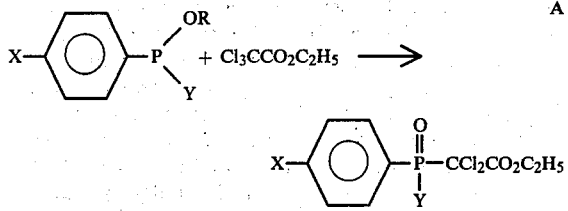

wherein
X is H or Cl
Y is —OR, —SR or $NR_2R_3$; and
R is an alkyl residue.

It has been demonstrated however, by several chemists that procedures like that described in Equation 1 do not give compounds of Formula A [Frieder W. Lichtenthaler, *Chemical Reviews*, 61, 612 (1961); and references cited therein]. The compounds produced by this type of procedure have been shown to have the structure described in Formula B.

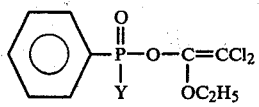

In U.S. Patent 2,995,486 compounds such as $$(EtO)_2PCCl_2CO_2Et,$$

are taught to be useful as insecticides.

Numerous compounds have been disclosed within recent years which are active herbicides; the need still exists, however, for herbicides which are more active. The presence of undesired vegetation is very damaging to useful a crop such as soybeans. In the current world situation, wherein food shortages are acute, it is most important not to lose a significant portion of a valuable crop such as soybeans. The presence of undesired vegetation results in the loss of a significant portion of such a crop. Thus, the need exists for a particularly effective herbicide which will destroy as much of this unwanted vegetation as is possible without causing significant damage to the desired crop, e.g. soybeans.

According to the instant invention, compounds have been discovered which are highly active herbicides and yet cause minimal damage to certain desired crops, e.g., cotton, soybeans and sugarbeets.

DESCRIPTION OF THE INVENTION

This invention relates to the novel compounds of Formula I and to agricultural compositions containing them, and to the method of use of these compounds as selective, as well as general, herbicides having both pre- and post-emergence activity:

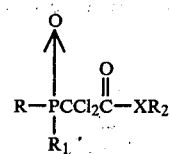

wherein
X is oxygen or sulfur;
$R_1$ is alkyl of 1-4 carbons, alkenyloxy of 3-4 carbons, phenyl, alkylthio of 1-3 carbons, alkoxy of 1-4 carbons, alkoxy of 2-3 carbons substituted with alkoxy of 1-3 carbons or with 1-3 chlorines or with one bromine, $NR_{11}R_{12}$, or phenoxy(optionally substituted with 1-3 chlorines or 1-3 bromines, 1-2 alkyls of 1-4 carbons, or with $NO_2$);
$R_2$ is alkyl of 1-6 carbons, alkenyl of 3-4 carbons or cycloalkyl of $C_5$-$C_6$ optionally substituted with one methyl.
R is alkyl of 1-4 carbons, cycloalkyl of 5-8 carbons, alkylcycloalkyl of 6-8 carbons, cycloalkylalkyl of 6-7 carbons, alkenyl of 3-4 carbons, arylalkyl of 7-8 carbons, thienyl, naphthyl, biphenyl, or

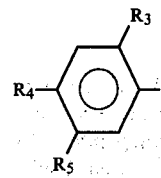

$R_3$ is hydrogen, chlorine, bromine, fluorine, nitro, methoxy, alkyl of 1-3 carbons;
$R_4$ is hydrogen, alkyl of 1-3 carbons, chlorine, bromine, fluorine, nitro, methoxy, —$NR_6R_7$ (where $R_6$ and $R_7$ are independently methyl or ethyl), $CO_2R_8$ where $R_8$ is alkyl of 1-3 carbons,

where $R_9$ and $R_{10}$ are independently hydrogen, methyl, or ethyl;
$R_5$ is hydrogen, chlorine, bromine, fluorine, nitro, $CF_3$, CN, alkyl of 1-3 carbons, alkoxy of 1-3 carbons

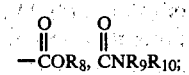

provided that:
(1) Only one of $R_3$, $R_4$, and $R_5$ can be $NO_2$ at the same time;
(2) When $R_4$ is

then $R_3$ and $R_5$ are H, Cl, or Br;

(3) When $R_5$ is other than H, Cl, Br, or F, then $R_3$ and $R_4$ are H, Cl, Br, or F; and (4) No more than two of $R_3$, $R_4$, or $R_5$ can be alkyl $C_1$–$C_3$, bromine or alkoxy at the same time.

$R_{11}$ is, alkyl of 1–4 carbons, cycloalkyl of 5–6 carbons, hydrogen or

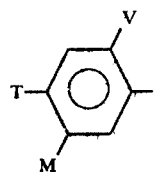

V is hydrogen, fluorine, chlorine, or nitro,

T is hydrogen, fluorine, chlorine, bromine, alkyl 1–3 carbons, or trifluoromethyl, and M is hydrogen, chlorine, alkoxy of 1–3 carbons, or trifluoromethyl provided that M and T are not simultaneously trifluoromethyl.

$R_{12}$ is H, methoxy or alkyl of 1–4 carbons, provided that when $R_{12}$ is methoxy $R_{11}$ is hydrogen or methyl; and $R_{11}$ and $R_{12}$ may also be taken together to form a bridge of the structure

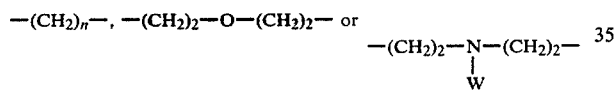

where n is 4–6 and W is H, methyl or ethyl.

Preferred in order of increasing activity and/or more favorable cost are independently or in combination:

(1) Compounds of Formula I wherein X is oxygen;

(2) Compounds of Formula I wherein R is $C_1$–$C_4$ alkyl or phenyl, especially the compounds of 1);

(3) Compounds wherein $R_1$ is $C_1$–$C_4$ alkoxy or $NR_{11}R_{12}$ wherein $R_{11}$ and $R_{12}$ are independently H or $C_1$–$C_4$ alkyl, especially the compounds of (1);

$R_{11}$ and $R_{12}$ may also be taken together to form a bridge of the structure

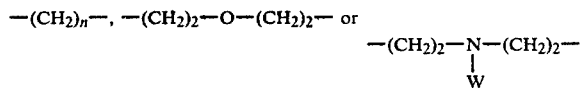

where n is 4–6 and W is H, methyl or ethyl;

(4) Compounds of (3) wherein R is $C_1$–$C_4$ alkyl or phenyl;

(5) Compounds of (4) wherein $R_1$ is alkoxy $C_1$–$C_4$;

(6) Compounds wherein $R_2$ is $C_1$–$C_4$ alkyl, especially the compounds of (1), (2), (3), (4), or (5).

Compounds of Formula I specifically preferred for their outstanding activity and/or very favorable cost are:

1-methylethyl 2,2-dichloro-2-[(1-methylethoxy)-phenylphosphinyl]acetate, m.p. 42°–44° C.

1-methylpropyl 2,2-dichloro-2-[(1-methylethoxy)-phenylphosphinyl]acetate.

1-methylethyl 2,2-dichloro-2-[(n-butoxy)phenylphosphinyl]acetate.

1-methylethyl 2,2-dichloro-2-[(1-methylethoxy)methylphosphinyl]acetate.

1-methylethyl 2,2-dichloro-2-[(ethoxy)methylphosphinyl]acetate.

1-methylethyl 2,2-dichloro-2-[(n-propoxy)phenylphosphinyl]acetate.

1-methylethyl 2,2-dichloro-2-[(ethoxy)ethylphosphinyl]acetate.

It is to be understood that all isomers of Formula I resulting from asymmetry at the phosphorous and/or carbon atoms are included within the scope of this invention.

METHODS OF PREPARATION

The compounds of Formula I can be prepared, as shown in Equation A, by chlorination of compounds of Formula II with a metal hypochlorite in aqueous media at a pH greater than seven, and a temperature between 0° and 75° C. U.S. Pat. No. 3,624,188 teaches a process for chlorination of phosphonoacetates in a two phase system consisting: (1) of an aqueous phase containing hypochlorite ion; and (2) an inert water-immiscible organic solvent phase in which the chlorinated products formed in the reaction are soluble to the extent of at least five percent by weight. Examples of such solvents are carbon tetrachloride, chloroform and sym-tetrachloroethane. It has been discovered that the compounds of the instant invention may be prepared by chlorination of a compound of Formula II with aqueous hypochlorite in the absence of a water-immiscible organic solvent phase. This process is an improvement over the prior art because it eliminates the need for the expensive and potentially toxic chlorinated hydrocarbon organic solvent.

EQUATION A

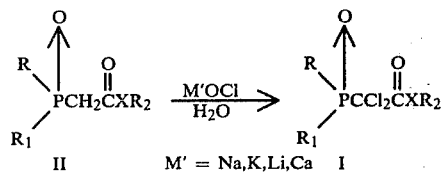

wherein R–$R_2$, and X are as previously defined.

Compounds of Formula I may also be prepared, as shown in Equation B, by chlorination of compounds of Formula II with sulfuryl chloride or with chlorine in the presence of actinic radiation as described in N. D. Bodnarchuk, V. V. Malovik, and G. I. Derkach J. Gen. Chem. (USSR) 39, 1673–1677 (1968) [CA 71, 12452e (1968)]. These reactions may be carried out either without solvent or with the addition of an appropriate inert solvent such as, for example, chloroform, carbon tetrachloride, benzene, or tetrachloroethane.

EQUATION B

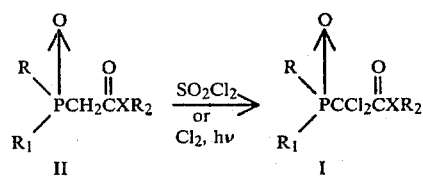

wherein R–R$_2$, and X are as previously defined.

The compounds of Formula II can be prepared, as shown in Equation C, by reaction of a phosphite of Formula III with an α-haloacetate of Formula IV as described in *Organophosphorus Compounds*—G. M. Kosolapoff, John Wiley and Sons, Inc. New York 1950, pp. 121–123. The reaction may be carried out at temperatures between 50° and 175° C., and either with or without an added inert organic solvent such as benzene, toluene, or xylene.

EQUATION C

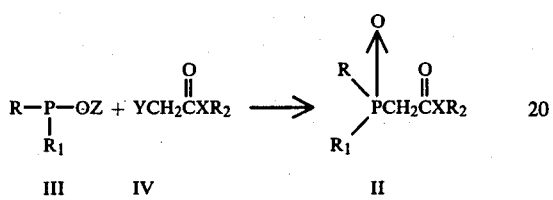

wherein R–R$_2$, and X are as previously defined Y is chlorine, bromine, or iodine; and Z is an alkyl group of one to six carbons.

Compounds of Formula III can be prepared by a suitable modification of the methods described in *Organophosphorus Compounds*—G. M. Kosolapoff, John Wiley and Sons Inc., New York, 1950, pp. 180–210, and *Organic Phosphorus Compounds*—Volume 4—G. M. Kosolapoff and L. Maier, John Wiley and Sons, Inc., 1972, pp. 255–462.

Typical examples of suitable methods for preparing compounds of Formula III are shown in Equations D, E, and F. The choice of the most suitable method will depend upon the exact nature of the substituents R$_3$–R$_5$, and will be obvious to one skilled in the art.

EQUATION D

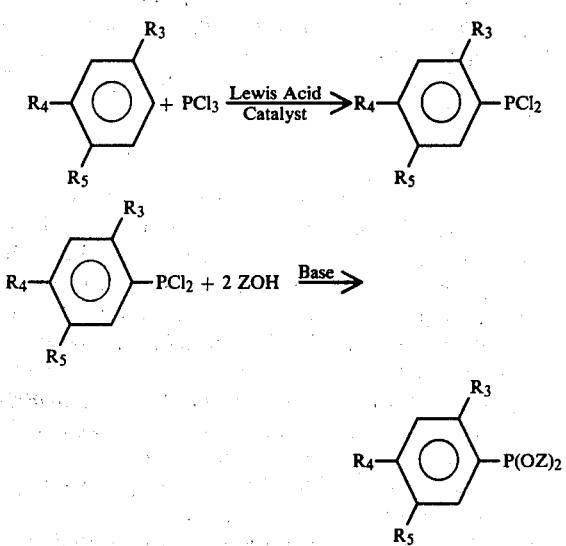

wherein R$_3$–R$_5$, and Z are as defined above.

EQUATION E

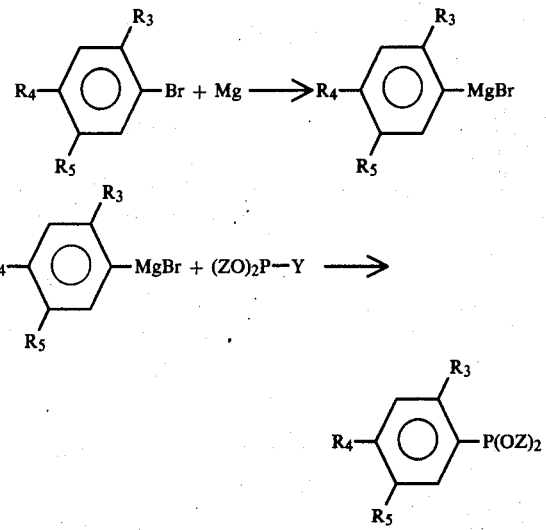

wherein R$_3$–R$_5$, Z and Y are as defined above.

EQUATION F

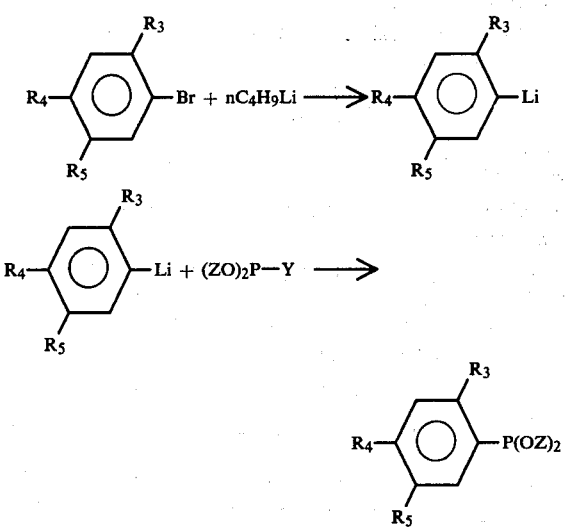

wherein R$_3$–R$_5$, Z, and Y are as defined above.

Certain compounds of Formula 1 can also be prepared by the method described in Equation G.

EQUATION G

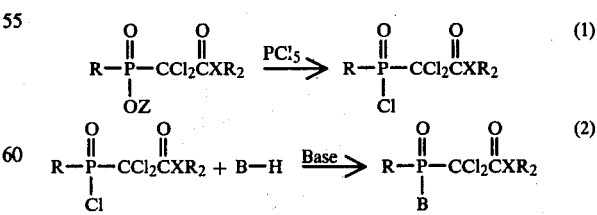

wherein R, R$_2$, X, and Z are as described above and B is an alkoxy, alkylthio, or phenoxy radical; or NR$_{11}$R$_{12}$ defined by R$_1$.

The chlorination reaction depicted in Equation G may be carried out at temperatures between 25° and

7

150° C. either with or in the absence of an added inert organic solvent such as carbontetrachloride, toluene, or chlorobenzene.

The second reaction in Equation G may be carried out at temperatures between about −78° and +80° C. in inert organic solvents such as diethylether, tetrahydrofuran, methylene chloride, or carbontetrachloride. Suitable bases include trialkyl amines; N,N-dialkyl anilines, metal alkoxides, and sodium hydride. An excess of trialkyl amine may also be used in this reaction in place of the inert organic solvent.

The following examples specifically illustrate this invention. Unless otherwise indicated, all parts are by weight and all temperatures in °C. Proton NMR data were obtained at 60 MHz and ambient temperature.

EXAMPLE 1

To a solution of 269 g of phenyl dichloro phosphine in 1.5 liters of tetrahydrofuran at 0°–10°, was added a solution of 180 g of 2-propanol and 310 g of triethylamine in 300 ml of tetrahydrofuran. After stirring for 2 hours at room temperature, the mixture was filtered and the filtrate concentrated in vacuo. The residue was distilled to give 209 g of diisopropyl phenylphosphite as a colorless oil bp 62°–63°/0.3 mm Hg.

NMR (CDCl$_3$)δ: 1.2–1.6 (m, 12.0H); 4.2–4.7 (m, 1.9H); 7.6–8.2 (m, 5.1H).

EXAMPLE 2

To 11.8 g of isopropyl bromoacetate was added 15.0 g of diisopropyl phenylphosphite at 80°–110°, while distilling off isopropyl bromide. The reaction mixture was heated to 130° over 30 minutes. Volatile products were removed under 10 mm vacuum at 65°. The yield of 1-methylethyl 2[(1-methylethoxy)phenylphosphinyl]acetate was 18.8 g as a colorless oil.

NMR (CDCl$_3$)δ: 1.1–1.6 (m, 12.1H); 3.2 (d, J=17 Hz, 1.7H); 4.6–5.4 (m, 1.8H); 7.7–8.5 (m, 5.3H).

EXAMPLE 3

A 5.25% commercial grade sodium hypochlorite solution (185 ml—Clorox ®) was cooled to 10° and the pH adjusted to 9.0 with 1 N HCl solution. To this solution, 15.0 g of 1-methylethyl 2[(1-methylethoxy)phenylphosphinyl]acetate was added at 10°–15° with vigorous stirring. The pH was kept between 9.0 and 9.5 by simultaneous addition of 1 N HCl solution (80 ml). The solution was stirred an additional 15 minutes at 15° then extracted with methylene chloride. The methylene chloride solution was dried and stripped to yield 17.0 g of 1-methylethyl 2,2-dichloro-2-[(1-methylethoxy)-phenylphosphinyl]acetate as a light yellow oil.

NMR (CDCl$_3$)δ: 1.3–1.7 (m, 12.3H); 5.0–5.6 (m, 1.8H); 7.7–8.6 (m, 4.9H).

Anal. Calc'd. for C$_{14}$H$_{19}$Cl$_2$O$_4$P: C, 47.61; H, 5.42; Cl, 20.08.

Found: C, 47.21; H, 5.24, 47.05 4.98. Cl, 20.44 20.38.

A sample of this oil slowly crystallized upon standing. It was recrystallized from cyclohexane to give a white solid, m.p. 42°–44°.

EXAMPLE 4

A solution of 20.4 g of 2-ethylbromobenzene in 50 ml of diethylether was added dropwise to 2.7 g of magnesium turnings in a nitrogen atmosphere. After the addition of the first 2 ml of this solution, 0.5 ml of 1,2-dibromoethane in 5 ml of diethylether was added to initiate the reaction. After initiation the remainder of the addition was carried out at 15° over a 1 hour period. After standing an additional 1 hour, the solution was filtered and added dropwise over 30 minutes to a solution of 15.6 g of diethyl chlorophosphite in 50 ml of ether at −60°. After standing an additional hour the solution was filtered and the salts washed with petroleum ether. The filtrate was stripped and the residue distilled to give 7.0 g of diethyl 2-ethylphenylphosphite, bp 65°/1.5 mm Hg.

NMR (CDCl$_3$)δ: 1.25 (t, 9H); 2.85 (q, 2H); 3.8 (m, 4H); 7.25–7.65 (m, 4H).

EXAMPLE 5

A solution of 176 ml of a 1.6 M solution of n-butyl lithium in hexane was added under a nitrogen atmosphere to a solution of 26.2 g of 2-fluorobromobenzene in 300 ml of diethylether at −65°. After stirring an additional 90 minutes at −65°, 28.0 g of diethyl chlorophosphite was added over a four minute period while holding the temperature below −48°. The reaction mixture was stirred at room temperature for 60 hours then refluxed for 30 minutes. The reaction mixture was then filtered and stripped to give an oil. Distillation yielded 10.2 g of diethyl 2-fluorophenylphosphite, bp 75°–79°/1.3 mm Hg.

NMR (CDCl$_3$)δ: 1.3 (t, 6H); 4.1 (m, 4H); 7.6 (m, 4H).

EXAMPLE 6

To 10.14 g of 1-methylethyl 2,2-dichloro-2-[(ethoxy)-phenylphosphinyl]acetate at 60° C. and under a nitrogen atmosphere was added 6.24 g of phosphorus pentachloride in 1 g portions over a 72 hour period. The mixture was stirred an additional 48 hours after addition. Volatile reaction products were distilled at 45°–50° C./0.75 mm Hg leaving 1-methylethyl 2,2-dichloro-2-[(1-chloro)phenylphosphinyl]acetate as a brown oil.

NMR (CDCl$_3$)δ: 1.3 (d, J=3.3H$_3$, 6H); 5.2 (m, 1H); 7.4–8.4 (m, 5H).

EXAMPLE 7

A solution of 11.7 g of diethylamine in 100 ml of diethylether is added dropwise to a solution of 27.1 g of 1-methylethyl 2,2-dichloro-[(1-chloro)phenylphosphinyl]-acetate in 200 ml of ether at 0°. After stirring at room temperature for 1 hour, the solution is washed with water and with 10% sodium bicarbonate solution, then dried over MgSO$_4$ and stripped to give a dark oil. The reaction product is dissolved in n-butyl chloride, washed with water, contacted with activated carbon, dried over MgSO$_4$ and stripped to give substantially pure 1-methylethyl 2,2-dichloro-[(diethylamino)phenylphosphinyl]acetate.

Using suitable modifications, of the procedures described in the above examples, the compounds of Formula I shown in Table 1 can be prepared.

TABLE 1

$$\begin{array}{c} R \quad O \quad O \\ \diagdown \parallel \quad \parallel \\ P-CCl_2CXR_2 \\ / \\ R_1 \end{array}$$

| R | $R_1$ | X | $R_2$ | $N_D$ | $\nu_{>C=O}(cm^{-1})$ |
|---|---|---|---|---|---|
|  | $CH_3O-$ | O | $nC_4H_9\underset{\mid}{C}H-$ <br> $CH_3$ | | |
|  | $(CH_3)_2CHO-$ | O | $(CH_3CH_2)_2CH-$ | 1.5013(25°) | |
|  | $(CH_3)_2CHO-$ | O | $C_2H_5-$ | 1.5126(27°) | 1745 |
|  | $(CH_3)_2CHO-$ | O | $C_2H_5\underset{\mid}{C}H-$ <br> $CH_3$ | 1.5070(27°) | 1745 |
|  | $CH_2=\underset{\mid}{C}-CH_2O-$ <br> $CH_3$ | O | $(CH_3)_2CH-$ | | |
|  | $n-C_6H_{13}O-$ | O | $C_2H_5-$ | | |
|  | $(CH_3)_2CHO-$ | O | $(CH_3)_2CH\underset{\mid}{C}H-$ <br> $CH_3$ | 1.5054(25°) | |
| 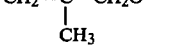 | $(CH_3)_2CHO-$ | O | $CH_2=CH-\underset{\mid}{C}H-$ <br> $CH_3$ | 1.5121(25°) | |
|  | $(CH_3)_2CHO-$ | S | $(CH_3)_2CH-$ | 1.5420(25°) | |
|  | $(CH_3)_2CHO-$ | S | $C_2H_5\underset{\mid}{C}H-$ <br> $CH_3$ | 1.5382(25°) | |
|  | $CH_3$ <br> $\mid$ <br> $C_2H_5CHO-$ | O | $CH_3$ <br> $\mid$ <br> $C_2H_5CH-$ | 1.5048(25°) | |
|  | $CH_3CH_2O-$ | O | $CH_2=CHCH_2-$ | 1.5315(26°) | 1770 |
|  | $(CH_3)_2CHO-$ | O | $CH_3$ <br> $\mid$ <br> $CH_2=C-CH_2-$ | 1.5243(25°) | 1760 |
|  | $nC_4H_9O-$ | O | $(CH_3)_2CH-$ | 1.5117(23.5°) | 1780 |
|  | $n-C_3H_7O-$ | O | $(CH_3)_2CH-$ | 1.5121(25°) | 1780 |
|  | $(CH_3)_2CHO-$ | O | $CH_3-$ | 1.5190(28°) | 1770 |
|  | $CH_3O-$ | O | $(CH_3)_2CH-$ | 1.5210(26°) | 1770 |
| 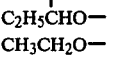 | $CH_3CH_2O-$ | O | $(CH_3)_2CH-$ | 1.5178(26°) | 1770 |
|  | $CH_3CH_2O-$ | O | $CH_3CH_2-$ | 1.5240(26°) | 1780 |
|  | $(CH_3)_2CHO-$ | O | $nC_3H_7\underset{\mid}{C}H-$ <br> $CH_3$ | 1.4950(26°) | |
|  | $CH_3S-$ | O | $(CH_3)_2CH-$ | | |
|  | $(CH_3)_2CHS-$ | O | $(CH_3)_2CH-$ | | |
|  | $(CH_3)_2CHS-$ | S | $(CH_3)_2CH-$ | | |
|  |  | O | $(CH_3)_2CH-$ | mp 71°–74° | |
|  | $CH_3-$ | O | $C_2H_5\underset{\mid}{C}H-$ <br> $CH_3$ | | |

TABLE 1-continued $$\underset{R_1}{\overset{R}{\vphantom{|}}}\!\!\underset{\|}{\overset{O}{P}}\!\!-\!\!CCl_2\overset{O}{\overset{\|}{C}}XR_2$$

| R | R₁ | X | R₂ | N_D | ν>C=O(cm⁻¹) |
|---|---|---|---|---|---|
| 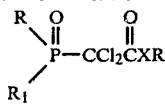 | (CH₃)₂CHCH₂O— | O | C₂H₅CH—<br>    \|<br>    CH₃ | 1.5052(25°) | |
|  | (CH₃)₃CO— | O | (CH₃)₂CH— | | |
|  | C₂H₅— | O | C₂H₅CH—<br>    \|<br>    CH₃ | | |
|  | CH₃<br> \|<br>CH₃CH₂CH— | O | (CH₃)₂CH— | | |
|  | CH₃O(CH₂)₃O— | O | (CH₃)₂CH— | | |
|  | ClCH₂CH₂O— | O | (CH₃)₂CH— | | |
|  | BrCH₂CH₂CH₂O— | O | CH₃<br> \|<br>CH₃CH₂CH— | 1.5359(25°) | |
|  | Cl₃CCH₂O— | O | C₂H₅CH—<br>    \|<br>    CH₃ | | |
|  | —O— | O | (CH₃)₂CH— | | |
|  | Cl——O— | O | (CH₃)₂CH— | | |
|  | Cl——O—<br>    Cl | O | (CH₃)₂CH— | | |
|  | Br—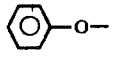—O—<br>(Br)(Br) | O | (CH₃)₂CH— | | |
|  | CH₃—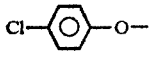—O— | S | (CH₃)₂CH— | | |
|  | NO₂<br> \|<br>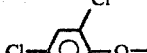—O—<br>CH₃ | O | (CH₃)₂CH— | | |
|  | (CH₃)₃C—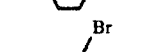—O— | O | (CH₃)₂CH— | | |
|  | 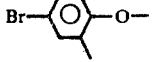—O—<br>    Cl | O | (CH₃)₂CH— | 1.5612(25°) | |
|  | CH₃ONH— | O | C₂H₅CH—<br>    \|<br>    CH₃ | | |
| 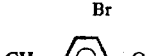 | CH₃O—N—<br>    \|<br>    CH₃ | O | C₂H₅CH—<br>    \|<br>    CH₃ | | |
|  | (CH₃)₂N— | O | (CH₃)₂CH— | | |
| 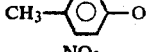 | (nC₄H₉)₂N— | O | (CH₃)₂CH— | | |
|  | (CH₃)₂CH—NH— | O | C₂H₅CH—<br>    \|<br>    CH₃ | | |

TABLE 1-continued $$\underset{R_1}{\overset{R}{\underset{\|}{\text{P}}}}\overset{O}{\underset{\|}{\text{—}}}CCl_2\overset{O}{\underset{\|}{\text{C}}}XR_2$$

| R | R₁ | X | R₂ | N_D | ν>c=o(cm⁻¹) |
|---|---|---|---|---|---|
| C₆H₅ | piperidin-N-yl | O | (CH₃)₂CH— | | |
| C₆H₅ | morpholin-N-yl | O | (CH₃)₂CH— | 1.5192(25°) | |
| C₆H₅ | 4-methylpiperazin-N-yl (CH₃N–N—) | O | (CH₃)₂CH— | | |
| C₆H₅ | [(CH₃)₂CH]₂N— | O | (CH₃)₂CH— | | |
| C₆H₅ | (C₂H₅)₂N— | O | C₂H₅CH(CH₃)— | | |
| C₆H₅ | pyrrolidin-N-yl | O | (CH₃)₂CH— | | |
| C₆H₅ | hexahydroazepin-N-yl | O | (CH₃)₂CH— | | |
| C₆H₅ | (CH₃)₃CNH— | O | (CH₃)₂CH— | | |
| C₆H₅ | (CH₃)₂N— | S | (CH₃)₂CH— | | |
| C₆H₅ | (CH₃)₂N— | O | CH₂=CH—CH(CH₃)— | | |
| C₆H₅ | C₆H₅—NH— | O | (CH₃)₂CH— | | |
| C₆H₅ | C₆H₅—N(CH₃)— | O | (CH₃)₂CH— | | |
| C₆H₅ | 2,4-dichlorophenyl-NH— | O | (CH₃)₂CH— | | |
| C₆H₅ | 4-CH₃-C₆H₄-NH— | O | (CH₃)₂CH— | | |
| C₆H₅ | 3-CF₃-C₆H₄-NH— | O | (CH₃)₂CH— | | |
| C₆H₅ | 4-Cl-2-NO₂-C₆H₃-NH— | O | (CH₃)₂CH— | | |
| C₆H₅ | 2-Cl-C₆H₄-NH— | O | (CH₃)₂CH— | | |
| C₆H₅ | 3-NO₂-C₆H₄-NH— | O | (CH₃)₂CH— | | |
| C₆H₅ | 2-Cl-C₆H₄-NH— | O | (CH₃)₂CH— | | |

TABLE 1-continued $$\begin{array}{c} R \quad O \quad O \\ \phantom{R_1}\diagdown \| \quad \| \\ \phantom{R_1} P-CCl_2CXR_2 \\ \phantom{RRR} / \\ R_1 \end{array}$$

| R | $R_1$ | X | $R_2$ | $N_D$ | $\nu>c=o(cm^{-1})$ |
|---|---|---|---|---|---|
| C6H5– | Cl–C6H4–NH– | O | $(CH_3)_2CH-$ | | |
| Cl–C6H4– | $CH_3CH_2O-$ | O | $CH_3CH_2-$ | 1.5223(27°) | |
| Cl–C6H4– | $CH_3CH_2O-$ | O | $(CH_3)_2CH-$ | 1.5250(27°) | |
| Cl–C6H4– | $(CH_3)_2CHO-$ | O | $(CH_3)_2CH-$ | 1.5169(27°) | |
| Cl–C6H4– | $(CH_3)_2CHO-$ | O | $C_2H_5CH(CH_3)-$ | 1.5164(27°) | |
| Br–C6H4– | $CH_3CH_2O-$ | O | $(CH_3)_2CH-$ | 1.5349(25°) | |
| 3,4-Cl2–C6H3– | $CH_3CH_2O-$ | O | $(CH_3)_2CH-$ | 1.5323(25°) | |
| 2-Cl-C6H3– | $CH_3CH_2O-$ | O | $(CH_3)_2CH-$ | 1.5442(25°) | |
| 4-(CH3)2N–C6H4– | $(CH_3)_2CHO-$ | O | $(CH_3)_2CH-$ | 1.5142(24°) | 1750 |
| 2,4-(CH3)2–C6H3– | $(CH_3)_2CHO-$ | O | $(CH_3)_2CH-$ | 1.5051(23°) | 1725 |
| 4-C2H5–C6H4– | $(CH_3)_2CHO-$ | O | $(CH_3)_2CH-$ | 1.5028(23°) | 1745 |
| 4-CH3–C6H4– | $(CH_3)_2CHO-$ | O | $(CH_3)_2CH-$ | 1.4938(24°) | 1750 |
| 4-(CH3)2CH–C6H4– | $CH_3CH_2O-$ | O | $(CH_3)_2CH-$ | 1.5175(27°) | 1725 |
| 2-C2H5–C6H4– | $(CH_3)_2CHO-$ | O | $(CH_3)_2CH-$ | | |
| 2-NO2–C6H4– | $(CH_3)_2CHO-$ | O | $(CH_3)_2CH-$ | 1.5148(22°) | |
| 4-NO2–C6H4– | $(CH_3)_2CHO-$ | O | $(CH_3)_2CH-$ | | |
| 2-NO2-4-CH3–C6H3– | $(CH_3)_2CHO-$ | O | $(CH_3)_2CH-$ | | |
| 2-F–C6H4– | $CH_3CH_2O-$ | O | $(CH_3)_2CH-$ | 1.5284(25°) | |
| 3-F–C6H4– | $CH_3CH_2O-$ | O | $(CH_3)_2CH-$ | 1.5018(25°) | |

TABLE 1-continued $$\underset{R_1}{\overset{R}{\underset{\|}{P}}}\overset{O}{\underset{\|}{-}}CCl_2\overset{O}{\underset{\|}{C}}XR_2$$

| R | R₁ | X | R₂ | $N_D$ | $\nu_{>C=O}(cm^{-1})$ |
|---|---|---|---|---|---|
| 4-F-C₆H₄- | CH₃CH₂O— | O | (CH₃)₂CH— | 1.5037(25°) | |
| 4-Me₂N-C₆H₄- | CH₃CH₂O— | O | (CH₃)₂CH— | | |
| 3-Cl-C₆H₄- | CH₃CH₂O— | O | (CH₃)₂CH— | 1.5235(25°) | |
| 2,4-Cl₂-C₆H₃- | CH₃CH₂O— | O | (CH₃)₂CH— | 1.5238(25°) | |
| 2-Br-C₆H₄- | CH₃CH₂O— | O | (CH₃)₂CH— | 1.5284(25°) | |
| 4-(C₂H₅OC(O))-C₆H₄- | (CH₃)₂CHO— | O | (CH₃)₂CH— | | |
| 4-((CH₃)₂NC(O))-C₆H₄- | (CH₃)₂CHO— | O | (CH₃)₂CH— | | |
| 4-(CH₃(C₆H₅)NC(O))-C₆H₄- | (CH₃)₂CHO— | O | (CH₃)₂CH— | | |
| 2-O₂N-C₆H₄- | (CH₃)₂N— | O | (CH₃)₂CH— | | |
| 3-O₂N-C₆H₄- | C₆H₅-O— | O | (CH₃)₂CH— | | |
| 2,4-Cl₂-C₆H₃- | (CH₃)₂N— | O | (CH₃)₂CH— | | |
| C₆H₅- | CH₂=CHCH₂O— | O | (CH₃)₂CH— | | |
| C₆H₅- | NH₂— | O | (CH₃)₂CH— | | |
| 2,4-Cl₂-C₆H₃- | C₆H₅-O— | O | (CH₃)₂CH— | | |
| 2,4-(CH₃)₂-C₆H₃- | 2-NO₂-4-CH₃-C₆H₃-O— | O | (CH₃)₂CH— | | |
| 3-Cl-C₆H₄- | (CH₃)₂CHS— | O | (CH₃)₂CH— | | |
| 3-F-C₆H₄- | (CH₃)₂N— | S | (CH₃)₂CH— | | |

TABLE 1-continued $$\begin{array}{c} R \diagdown \overset{O}{\underset{\|}{P}} - CCl_2 \overset{O}{\underset{\|}{C}} XR_2 \\ R_1 \end{array}$$

| R | $R_1$ | X | $R_2$ | $N_D$ | $\nu_{>C=O}(cm^{-1})$ |
|---|---|---|---|---|---|
| $C_2H_5O\overset{O}{\underset{\|}{C}}$—〈phenyl〉— | $(CH_3)_2N$— | O | $(CH_3)_2CH$— | | |
| $(CH_3)_2N\overset{O}{\underset{\|}{C}}$—〈phenyl〉— | $(CH_3)_2N$— | O | $(CH_3)_2CH$— | | |
| $CH_3$— | $(CH_3)_2CHO$— | O | $(CH_3)_2CH$— | 1.4590(23°) | 1750 |
| $CH_3$— | $CH_3CH_2O$— | O | $(CH_3)_2CH$ | 1.4587(22.5) | 1770 |
| $C_2H_5$— | $CH_3CH_2O$— | O | $(CH_3)_2CH$ | 1.4652(26°) | 1780 |
| $C_2H_5$— | $(CH_3)_2CHO$— | O | $(CH_3)_2CH$— | 1.4612(26°) | 1780 |
| $(CH_3)_3C$— | $CH_3O$— | O | $C_2H_5-\underset{\underset{CH_3}{\|}}{CH}-$ | 1.4757(22°) | |
| $C_2H_5$— | $C_2H_5$— | O | $C_2H_5-\underset{\underset{CH_3}{\|}}{CH}-$ | 1.4585(22°) | |
| $C_2H_5$— | $n\text{-}C_4H_9O$— | O | $C_2H_5-\underset{\underset{CH_3}{\|}}{CH}-$ | 1.4611(22°) | |
| 〈thienyl〉— | $C_2H_5O$— | O | $C_2H_5-\underset{\underset{CH_3}{\|}}{CH}-$ | 1.5200(21°) | |
| $CH_3$— | $(CH_3)_2N$— | O | $(CH_3)_2CH$— | | |
| 〈thienyl〉— | $(CH_3)_2N$— | O | $(CH_3)_2CH$— | | |
| 〈phenyl〉— | $CH_3$— | O | $(CH_3)_2CH$ | | |
| 〈naphthyl〉— | $(CH_3)_2CHO$— | O | $(CH_3)_2CH$— | | |
| 〈thienyl〉— | $(CH_3)_2CHO$— | O | $(CH_3)_2CH$— | | |
| 〈thienyl〉— | $(CH_3)_2N$— | O | $(CH_3)_2CH$— | | |
| 〈thienyl〉-$CH_2$— | $(CH_3)_2CHO$— | O | $(CH_3)_2CH$— | | |
| 〈methylthienyl〉— | $(CH_3)_2CHO$— | O | $(CH_3)_2CH$— | | |
| 〈phenyl〉-$CH_2$— | $(CH_3)_2CHO$— | O | $(CH_3)_2CH$— | | |
| 〈phenyl〉-$CH_2$— | $(CH_3)_2N$— | O | $(CH_3)_2CH$— | | |
| $(CH_3)_3C$— | $(CH_3)_2N$— | O | $(CH_3)_2CH$— | | |
| $CH_3$— | $CH_3$— | O | $(CH_3)_2CH$— | | |
| 〈phenyl〉— | $(CH_3)_2CH$— | O | $(CH_3)_2CH$— | | |
| 〈naphthyl〉— | $(CH_3)_2N$— | O | $(CH_3)_2CH$— | | |
| $(CH_3)_3C$— | $(CH_3)_2CHS$— | O | $(CH_3)_2CH$— | | |
| 〈phenyl〉— | $(CH_3)_2CHO$— | O | $n\text{-}C_3H_7\underset{\underset{CH_3}{\|}}{CH}CH-$ | | |
| 〈phenyl〉— | $(CH_3)_2CHO$— | O | $(C_2H_5)_2CH$— | | |

TABLE 1-continued $$\begin{array}{c} R \quad O \quad O \\ \quad \backslash \parallel \quad \parallel \\ \quad P-CCl_2CXR_2 \\ \quad / \\ R_1 \end{array}$$

| R | $R_1$ | X | $R_2$ | $N_D$ | $\nu >C=O (cm^{-1})$ |
|---|---|---|---|---|---|
| C₆H₅ | (CH₃)₂CHO— | O | (CH₃)₂CHCH—<br>    \|<br>    CH₃ | | |
| C₆H₅ | (CH₃)₂CHO— | O | (2-thienyl) | | |
| C₆H₅ | (CH₃)₂CHOCH₂CH₂CH₂O— | O | (CH₃)₂CH— | | |
| C₆H₅ | (CH₃)₂CHOCH₂CH₂O— | O | (CH₃)₂CH— | | |
| C₆H₅ | C₂H₅OCH₂CH₂CH₂O— | O | (CH₃)₂CH— | | |
| C₆H₅ | C₂H₅OCH₂CH₂O— | O | (CH₃)₂CH— | | |
| C₆H₅ | CH₃OCH₂CH₂O— | O | (CH₃)₂CH— | | |
| C₆H₅ | n-C₃H₇CHO—<br>      \|<br>      CH₃ | O | C₂H₅CH—<br>    \|<br>    CH₃ | 1.4940(25°) | |
| C₆H₅ | n-C₄H₉CHO—<br>      \|<br>      CH₃ | O | C₂H₅CH—<br>    \|<br>    CH₃ | 1.4941(25°) | |
| C₆H₅ | CH₃OCH₂CH₂O— | O | C₂H₅CH—<br>    \|<br>    CH₃ | 1.5059(25°) | |
| CH₃— | CH₃O— | O | C₂H₅CH—<br>    \|<br>    CH₃ | 1.4678(25°) | |
| C₂H₅— | CH₃O— | O | C₂H₅CH—<br>    \|<br>    CH₃ | 1.4665(25°) | |
| C₂H₅— | CH₃OCH₂CH₂CH₂O— | O | C₂H₅CH—<br>    \|<br>    CH₃ | 1.4590(25°) | |
| C₆H₅CH₂— | C₂H₅O— | O | (CH₃)₂CH— | 1.5080 | 1750 |
| C₆H₅CH₂— | (CH₃)₂CHO— | O | C₂H₅CH—<br>    \|<br>    CH₃ | | |
| C₂H₅— | (C₂H₅)₂N— | O | (CH₃)₂CH— | 1.4810 | |
| n-C₄H₉— | (C₂H₅)₂N— | O | (CH₃)₂CH— | 1.4717 | |
| CH₃— | (C₂H₄)₂N— | O | (CH₃)₂CH— | 1.4733 | |
| C₆H₅ | C₆H₅ | O | C₂H₅CH—<br>    \|<br>    CH₃ | m.p. 75°–78° | |
| 2-CH₃-C₆H₄ | C₂H₅O— | O | (CH₃)₂CH— | 1.5131 | 1750 |
| 4-CH₃-C₆H₄ | C₂H₅O— | O | (CH₃)₂CH— | 1.5181 | 1750 |
| 2,3-Cl₂-C₆H₃ | C₂H₅O— | O | (CH₃)₂CH— | 1.5328 | |
| 2-OCH₃-C₆H₄ | C₂H₅O— | O | (CH₃)₂CH— | 1.5178 | 1745 |
| 4-CH₃O-C₆H₄ | C₂H₅O— | O | (CH₃)₂CH— | | |
| C₆H₅ | (CH₃)₂CHO— | O | (2-thianyl) | | |

TABLE 1-continued $$\begin{array}{c} R \diagdown \underset{\|}{\overset{O}{P}} - CCl_2 \overset{O}{\overset{\|}{C}} XR_2 \\ R_1 \diagup \end{array}$$

| R | $R_1$ | X | $R_2$ | $N_D$ | $\nu > c = o (cm^{-1})$ |
|---|---|---|---|---|---|
|  | $(CH_3)_2CHO-$ | O |  CH$_3$ | | |
|  | $(CH_3)_2CHO-$ | O |  | | |

Useful formulations of the compounds of Formula I can be prepared in conventional ways. They include dusts, granules, pellets, solutions, emulsions, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Emulsions, Solutions (including Emulsifiable Concentrates) | 5–50 | 40–95 | 0–15 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.Y. The denser diluents are preferred for dusts. Typical liquid diluents and solvents are described in Marsden, "Solvents Guide", 2nd. Edn., Interscience, New York, 1950. Solution concentrates are preferably stable against phase separation at 0° C. "McCutcheon's Detergents and Emulsifiers Annual", Allured Publ. Corp., Ridgwood, New Jersey, as well as Sisely and Wood, "Encyclopedia of Surface Active Agents", Chemical Publ. Co., Inc. New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 4th. Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5 Line 43, through Col. 7, Line 62 and Ex. 8, 12, 15, 39, 41, 52, 53, 58, 132, 138–140, 162–164, 166, 167, and 169–182.

H. Gysin and E. Knüsli, U.S. Pat. No. 2,891,855, June 23, 1959, Col. 3 Line 66 through Col. 5, Line 17 and Examples 1–4.

G. C. Klingman, "Weed Control as a Science". John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

EXAMPLE 8

Emulsifiable Concentrate

| | |
|---|---|
| 1-methylethyl 2,2-dichloro-2-[(n-butoxy)phenylphosphinyl]-acetate | 25% |
| blend of oil soluble sulfonates and polyoxyethylene ethers | 6% |
| cumene range aromatic solvent | 69% |

The ingredients are combined and stirred with gentle warming to speed solution. A fine screen filter is included in packaging operation to insure the absence of any extraneous undissolved material in the product.

EXAMPLE 9

Pellets—Granules

| | |
|---|---|
| 1-methylethyl 2,2-dichloro-2-(1-methylethoxy)phenylphosphinyl acetate | 15% |
| anhydrous sodium sulfate | 10% |
| crude calcium ligninsulfonate | 5% |
| sodium alkylnaphthalenesulfonate | 1% |
| calcium/magnesium bentonite | 69% |

The ingredients are blended and moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 10

Emulsifiable Concentrates

| | |
|---|---|
| 1-methylethyl 2,2-dichloro-2-[(1-methylethoxy)phosphinyl]acetate | 36% |
| blend of oil soluble sulfonates and polyoxyethylene ethers | 8% |
| 2-butoxyethanol | 56% |

The ingredients are combined and stirred until solution is effected. After filtration, the liquid may be used directly in LV or ULV applications or may be emulsified in water before spraying.

EXAMPLE 11

Granules

| | |
|---|---|
| 1-methylethyl 2,2-dichloro-2-[(ethoxy)ethylphosphinyl]acetate | 5% |
| preformed bentonite granules, 20-50 mesh | 95% |

The active ingredient is dissolved in isopropanol to make a 20% solution which is then sprayed on the preformed granules as they are tumbled in a double cone blender. After drying to remove solvent, the granules are packaged.

Utility

The compounds of the present invention are useful for the control of undesired vegetation. They can be used for the selective control of weeds in crops, such as cotton, soybeans and sugarbeets, or wherever general weed control is required, such as on industrial sites, railroad rights-of-way and locations adjacent to croplands.

The precise amount of the compounds of the present invention to be used in any given situation will vary according to the particular end result desired, the use involved, the plant and soil involved, the formulation used, the mode of application, prevailing weather conditions, foliage density and like factors. Since so many variables play a role, it is not possible to state a rate of application suitable for all situations. Broadly speaking, the compounds of the invention are used at levels of about 0.06 to about 15 kilograms per hectare. The lower rates in this range will generally be selected for selective weed control in crops, on lighter soils, soils low in organic matter content, or in situations where maximum persistance is not necessary. In many situations it is advantageous to incorporate these chemicals with the soil.

The compounds of the present invention may be combined with any other herbicide and they are particularly useful in combination with herbicides of the substituted urea, uracil or s-triazine types for controlling a broad spectrum of weeds.

The following herbicidal compounds may be used in combination with the compounds of the instant invention:

5-amino-4-chloro-2-phenyl-3(2H)-pyridazinone (Pyrazon)
2-chloro-4,6-bis(ethylamino)-s-triazine (Simazine)
2-chloro-4-(ethylamino)-6-(isopropylamino)-s-triazine (Atrazine)
2-chloro-4,6-bis(isopropylamino)-s-triazine (Propazine)
2-[[4-chloro-6-(ethylamino)-s-triazin-2-yl]amino]-2-methylproprionitrile (Cyanazine)
4-amino-6-(1,1-dimethylethyl)-3-(methylthio)-1,2,4-triazin-5(4H)-one (Metribuzin)
3-(3,4-dichlorophenyl)-1,1-dimethylurea (Diuron)
3-[p-(p-chlorophenoxy)phenyl]-1,1-dimethylurea (Chloroxuron)
1,1-dimethyl-3-($\alpha,\alpha,\alpha$-trifluoro-m-tolyl)urea (Fluormeturon)
3-(3,4-dichlorophenyl)-1-methoxy-1-methylurea (Linuron)
5-bromo-3-sec-butyl-6-methyluracil (Bromacil)
3-cyclohexyl-5,6-trimethyleneuracil (Lenacil)
2-chloro-1-(3-ethoxy-4-nitrophenoxy)-4-trifluoromethylbenzene
3-isopropyl-(1H)-2,1,3-benzothiadiazin-4(3H)-one, 2,2-dioxide (Bentazone)
1,1-dimethyl-4,4'-bipyridium ion (Paraquat)
2,4-dichlorophenoxy acetic acid and salts
5-[2-chloro-4-(trifluoromethyl)phenoxy]-2-nitrobenzoic acid, sodium salts (Blazer ®)

Herbicidal activity of the subject compounds was discovered in a number of greenhouse tests, as described below.

TEST A

Seeds of crabgrass (Digitaria spp.), barnyardgrass (Echinochloa crusgalli), wild oats (Avena fatua), cassia (Cassia tora), morningglory (Ipomoea hederacea), cocklebur (Xanthium spp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days, then all species were compared to controls and visually rated for response in treatment.

Ratings for compounds tested by this procedure are recorded in Table A. The ratings are based on a numerical scale extending from 0=no injury, to 10=complete kill. The accompanying letters have the following meanings: C=chlorosis/necrosis; B=burn; G=growth retardation; E=emergence inhibition; H=formative effects; X=axillary stimulation; 6Y=abscised buds or flowers; and 6F=delayed flowering.

TABLE A

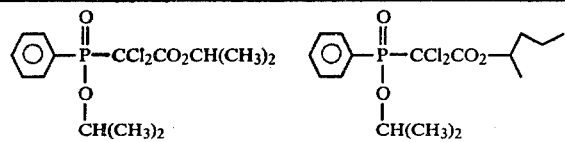

| kg/ha | 0.4 | 0.4 | 2 |
|---|---|---|---|
| POST EMERGENCE | | | |
| BUSH BEAN | 3H,6Y | | |
| COTTON | 3C,5G | | |
| MORNING GLORY | 4G | 2H | 1H |
| COCKLEBUR | 5X | 0 | 1H |
| CASSIA | 9G | 0 | 3H |
| NUTSEDGE | 8G | 0 | 5G |
| CRABGRASS | 9H | 6G | 1B,9G |
| BARNYARD GRASS | 9H | 4H | 9H |
| WILD OATS | 5G | 0 | 0 |
| WHEAT | 2C,7G | 0 | 5G,5X |
| CORN | 9H | 0 | 8H |
| SOYBEAN | 5H | 0 | 1B,3H |
| RICE | 5G | 0 | 3G |
| SORGHUM | 8G | 0 | 5G |
| PRE EMERGENCE | | | |
| MORNING GLORY | 0 | 0 | 0 |
| COCKLEBUR | 0 | | |
| CASSIA | 0 | 0 | 0 |
| NUTSEDGE | 9G,10C | 0 | 2G |
| CRABGRASS | 9H | 0 | 5G |
| BARNYARD GRASS | 10H | 8H | 9H |
| WILD OATS | 9H | 2G | 5G |
| WHEAT | 10H | 6G | 8G |
| CORN | 9H | 4H | 7H |
| SOYBEAN | 3H | 0 | 3G |
| RICE | 10E | 2G | 5G |
| SORGHUM | 10H | 2G | 7G |

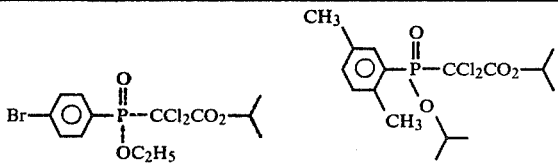

| kg/ha | 2 | 2 |
|---|---|---|
| POST EMERGENCE | | |
| BUSH BEAN | | |
| COTTON | 4B | 2B |
| MORNING GLORY | 1B | 1B |
| COCKLEBUR | 1H | 0 |
| CASSIA | 3H | 4H |
| NUTSEDGE | 3G | 0 |
| CRABGRASS | 1C,9G | 7G |
| BARNYARD GRASS | 7H | 6H |
| WILD OATS | 0 | 0 |
| WHEAT | 0 | 0 |
| CORN | 3H | 7H |
| SOYBEAN | 7G,5X | 2H,5G,5X |
| RICE | 2G | 5G |
| SORGHUM | 0 | 2G |
| PRE EMERGENCE | | |
| MORNING GLORY | 1H | 0 |
| COCKLEBUR | 0 | 0 |
| CASSIA | 0 | 0 |
| NUTSEDGE | 9G | 0 |
| CRABGRASS | 8H | 6G |
| BARNYARD GRASS | 9H | 9H |
| WILD OATS | 9H | 2G |
| WHEAT | 9H | 9H |
| CORN | 8H | 9H |
| SOYBEAN | 2G | 2G |
| RICE | 9G | 7G |
| SORGHUM | 8H | 5G |

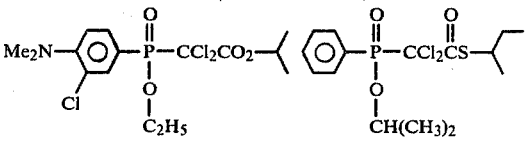

TABLE A-continued

| kg/ha | 2 | 0.4 | 2 |
|---|---|---|---|
| POST EMERGENCE | | | |
| BUSH BEAN |  | 1B | 9C |
| COTTON | 2B | 1B | 2C,8G |
| MORNING GLORY | 0 | 1B,4H | 10C |
| COCKLEBUR | 0 | 0 | 0 |
| CASSIA | 0 | 4G | 1C,6H |
| NUTSEDGE | 0 | 0 | 6G |
| CRABGRASS | 5G | 7G | 9G |
| BARNYARD GRASS | 3H | 1C,6H | 9H |
| WILD OATS | 0 | 0 | 2G |
| WHEAT | 0 | 0 | 2G |
| CORN | 0 | 0 | 7H |
| SOYBEAN | 1H,3X | 3G | 6H |
| RICE | 0 | 2G | 6G |
| SORGHUM | 0 | 0 | 5G |
| PRE EMERGENCE | | | |
| MORNING GLORY | 1H | 1H | 5H |
| COCKLEBUR | 0 | 0 | 0 |
| CASSIA | 0 | 9C | 10E |
| NUTSEDGE | 0 | 5G | 9G |
| CRABGRASS | 8H | 7H | 9H |
| BARNYARD GRASS | 9H | 9H | 9H |
| WILD OATS | 4H | 1H | 6H |
| WHEAT | 9H | 8H | 9H |
| CORN | 9H | 7H | 9H |
| SOYBEAN | 1H | 0 | 3H |
| RICE | 7G | 8G | 9H |
| SORGHUM | 3G | 8G | 9H |

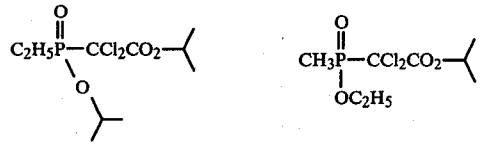

| kg/ha | 2 | 0.4 | 2 |
|---|---|---|---|
| POST EMERGENCE | | | |
| BUSH BEAN | 5H | 0 | 4G |
| COTTON | 1B,5H | 0 | 1B,2H |
| MORNING GLORY | 5H |  | 4H |
| COCKLEBUR | 2G | 0 |  |
| CASSIA | 1B,5H |  | 1H |
| NUTSEDGE | 2G | 0 | 0 |
| CRABGRASS | 8H | 5G | 8G |
| BARNYARD GRASS | 9H | 1H | 9H |
| WILD OATS | 0 | 0 | 7G |
| WHEAT | 4G | 0 | 7H |
| CORN | 9H | 6H | 9H |
| SOYBEAN | 6H | 5H | 7H |
| RICE | 10P,8G | 5G | 8G |
| SORGHUM | 1C,8H | 3G | 8H |
| PRE EMERGENCE | | | |
| MORNING GLORY | 8H |  |  |
| COCKLEBUR | 1H | 0 |  |
| CASSIA | 6H |  |  |
| NUTSEDGE | 10E | 9G | 10E |
| CRABGRASS | 10E | 9H | 10E |
| BARNYARD GRASS | 10H | 9H | 9H |
| WILD OATS | 9H | 9H | 9H |
| WHEAT | 10H | 9H | 9H |
| CORN | 10H | 9H | 9H |
| SOYBEAN | 9H | 6H | 9H |
| RICE | 10E | 9G | 10E |
| SORGHUM | 10H | 8H | 9H |

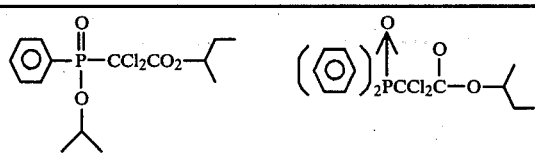

| kg/ha | 0.4 | 2 | 2/5 |
|---|---|---|---|
| POST EMERGENCE | | | |
| BUSH BEAN | 0 | 2B | 0 |
| COTTON | 1B,1H | 3B | 1B |
| MORNING GLORY | 0 | 1B | 0 |
| COCKLEBUR | 3G | 1B | 0 |
| CASSIA | 3H | 1B | 0 |

TABLE A-continued

| | | | |
|---|---|---|---|
| NUTSEDGE | 6G | 0 | 0 |
| CRABGRASS | 9G | 7G | 5G |
| BARNYARD GRASS | 2C,9H | 7H | 1H |
| WILD OATS | 0 | 0 | 0 |
| WHEAT | 3G | 0 | 0 |
| CORN | 8H | 0 | 0 |
| SOYBEAN | 4H | 1B | 0 |
| RICE | 2G | 0 | 0 |
| SORGHUM | 6G | 0 | 0 |
| PRE EMERGENCE | | | |
| MORNING GLORY | 0 | 0 | 0 |
| COCKLESBUR | 0 | 0 | — |
| CASSIA | 0 | 0 | 0 |
| NUTSEDGE | 10E | 6G | 0 |
| CRABGRASS | 10E | 9H | 7G |
| BARNYARD GRASS | 10H | 9H | 9H |
| WILD OATS | 9H | 4G | 0 |
| WHEAT | 9H | 9G | 9G |
| CORN | 9H | 9H | 8H |
| SOYBEAN | 0 | 0 | 0 |
| RICE | 10E | 1C,8G | 8G |
| SORGHUM | 9H | 9H | 7G |

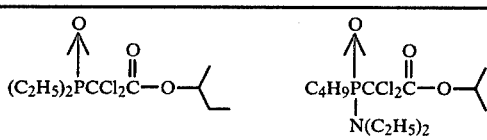

| kg/ha | 2 | 2 | 2/5 |
|---|---|---|---|
| POST EMERGENCE | | | |
| BUSH BEAN | 2G | 2B,5H | 2H |
| COTTON | 1B,5H | 5B,8H | 2B,2H |
| MORNING GLORY | 1H | 3B | 3H |
| COCKLEBUR | 0 | 3H,6F | 0 |
| CASSIA | 0 | 1B,5H | 2G |
| NUTSEDGE | 0 | 5G | 0 |
| CRABGRASS | 5H | 1B,9G | 9G |
| BARNYARD GRASS | 5H | 1B,9H | 7H |
| WILD OATS | 0 | 1B | 0 |
| WHEAT | 0 | 1B,5G | 0 |
| CORN | 3H | 9H | 0 |
| SOYBEAN | 1H,4G | 2B,7H | 5H |
| RICE | 0 | 1B,9G | 0 |
| SORGHUM | 2G | 1B,5G | 0 |
| PRE EMERGENCE | | | |
| MORNING GLORY | 1C,5G | 5H | 1C,3H |
| COCKLEBUR | 0 | 0 | — |
| CASSIA | 1C | 5H | 3H |
| NUTSEDGE | 6G | 10E | 7G |
| CRABGRASS | 10E | 9H | 8H |
| BARNYARD GRASS | 10H | 9H | 9H |
| WILD OATS | 8H | 7G | 2G |
| WHEAT | 9H | 9H | 9H |
| CORN | 9H | 9H | 9H |
| SOYBEAN | 7H | 9H | 8H |
| RICE | 10E | 9G | 9G |
| SORGHUM | 9H | 9H | 9H |

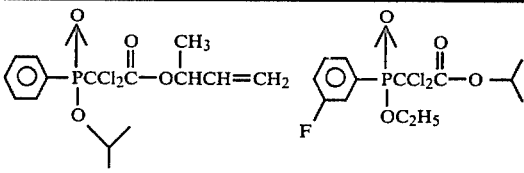

| kg/ha | 2 | 2/5 | 2/5 |
|---|---|---|---|
| POST EMERGENCE | | | |
| BUSH BEAN | — | — | 0 |
| COTTON | — | — | 1H |
| MORNING GLORY | 1B,3H | 2H | 2H |
| COCKLEBUR | 1H,6F | 0 | 0 |
| CASSIA | 1B,8H | 2H | 1H |
| NUTSEDGE | 8G | 8G | 6G,5X |
| CRABGRASS | 1B,8G | 8G | 2C,9H |
| BARNYARD GRASS | 9H | 9H | 3C,9H |
| WILD OATS | 7H | 1H,5I | 0 |
| WHEAT | 8H | 7H | 5G |
| CORN | 1B,9H | 9H | 5H |
| SOYBEAN | 1B,6H | 3H | 0 |

TABLE A-continued

| | | | |
|---|---|---|---|
| RICE | 1B,8G | 7G | 7G |
| SORGHUM | 1B,8H | 8H | 2H |
| PRE EMERGENCE | | | |
| MORNING GLORY | 1C,7G | 2H | 1C,5G |
| COCKLEBUR | — | — | 0 |
| CASSIA | 1C,7G | 3H | 1C,7G |
| NUTSEDGE | 10E | 10E | 10E |
| CRABGRASS | 10E | 9H | 10E |
| BARNYARD GRASS | 9H | 9H | 10H |
| WILD OATS | 9H | — | 9H |
| WHEAT | 9H | 9H | 9H |
| CORN | 9H | 9H | 9H |
| SOYBEAN | 8G | 4G | 7G |
| RICE | 9H | 9G | 10E |
| SORGHUM | 9H | 9H | 9H |

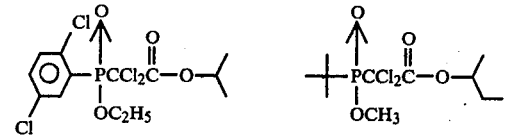

| kg/ha | 2 | 2 | 2/5 |
|---|---|---|---|
| POST EMERGENCE | | | |
| BUSH BEAN | 1B | 0 | 0 |
| COTTON | 2B,2H | 1B | 0 |
| MORNING GLORY | 1B | 2H | 0 |
| COCKLEBUR | 1B,6F | 1B | 0 |
| CASSIA | 1B,5H | 0 | 0 |
| NUTSEDGE | 2G | 0 | 0 |
| CRABGRASS | 9G | 3G | 0 |
| BARNYARD GRASS | 1B,8H | 3H | 0 |
| WILD OATS | 0 | 0 | 0 |
| WHEAT | 0 | 0 | 0 |
| CORN | 1B,5H | 0 | 0 |
| SOYBEAN | 1B,3G | 1H | 0 |
| RICE | 1B,6G | 0 | 0 |
| SORGHUM | 1B,4G | 0 | 0 |
| PRE EMERGENCE | | | |
| MORNING GLORY | 2G | 0 | 0 |
| COCKLEBUR | 0 | — | 0 |
| CASSIA | 0 | 0 | — |
| NUTSEDGE | 0 | 2G | 0 |
| CRABGRASS | 9H | 8H | 5H |
| BARNYARD GRASS | 10H | 9H | 9H |
| WILD OATS | 9H | 2G | 0 |
| WHEAT | 9H | 8G | 0 |
| CORN | 7H | 8H | 0 |
| SOYBEAN | 2G | 5G | 3H |
| RICE | 8G | 6G | 1H |
| SORGHUM | 9H | 6H | 0 |

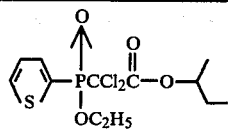

| kg/ha | 2 | 2/5 |
|---|---|---|
| POST EMERGENCE | | |
| BUSH BEAN | 3H | 2H |
| COTTON | 3C,3H | 3B,2H |
| MORNING GLORY | 2H | 1H |
| COCKLEBUR | 2H | 2G |
| CASSIA | 3H | 0 |
| NUTSEDGE | 1C,9G | 7G,5X |
| CRABGRASS | 1C,9G | 9G |
| BARNYARD GRASS | 9H | 9H |
| WILD OATS | 9H | 0 |
| WHEAT | 8G,5X | 3G,5X |
| CORN | 9H | 2G |
| SOYBEAN | 4H | 1H |
| RICE | 9G | 9G |
| SORGHUM | 9H | 4G |
| PRE EMERGENCE | | |
| MORNING GLORY | 2C,8G | 2C,2H |
| COCKLEBUR | 0 | 0 |
| CASSIA | 8G | 1C |
| NUTSEDGE | 10E | 7G |
| CRABGRASS | 10E | 10E |
| BARNYARD GRASS | 10H | 10H |

TABLE A-continued

| | | |
|---|---|---|
| WILD OATS | 9H | 9H |
| WHEAT | 9H | 9H |
| CORN | 9H | 8H |
| SOYBEAN | 4H | 2G |
| RICE | 10E | 9H |
| SORGHUM | 9H | 9H |

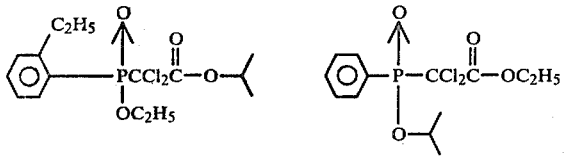

| kg/ha | 2 | 2/5 | 2/5 |
|---|---|---|---|
| POST EMERGENCE | | | |
| BUSH BEAN | — | — | 2H |
| COTTON | 3B,4G | — | 1C,3H |
| MORNING GLORY | 1B,4H | — | 1H |
| COCKLEBUR | 2G | — | 2G |
| CASSIA | 4H | — | 2G |
| NUTSEDGE | 7G | — | 0 |
| CRABGRASS | 1C,8G | — | 6H |
| BARNYARD GRASS | 1C,9H | — | 8H |
| WILD OATS | 1B,3H | — | 0 |
| WHEAT | 1B,7G,5X | — | 0 |
| CORN | 1B,8H | — | 0 |
| SOYBEAN | 1B,5H | — | 1H |
| RICE | 1B,7G | — | 0 |
| SORGHUM | 1B,7H | — | 0 |
| PRE EMERGENCE | | | |
| MORNING GLORY | 4G | — | 0 |
| COCKLEBUR | 0 | — | 0 |
| CASSIA | 1H | — | 0 |
| NUTSEDGE | 10E | 10E | 6G |
| CRABGRASS | 10E | 10E | 6G |
| BARNYARD GRASS | 10H | 9H | 10H |
| WILD OATS | 9H | 9H | 5G |
| WHEAT | 9H | 9H | 8G |
| CORN | 9H | 9H | 9H |
| SOYBEAN | 5H | — | 0 |
| RICE | 10E | 9H | 9E,8G |
| SORGHUM | 9H | 9H | 7H |

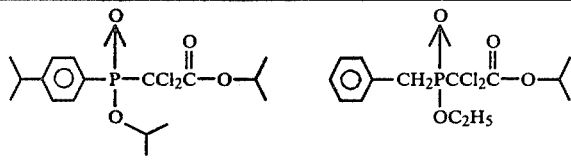

| kg/ha | 2 | 2/5 | 2/5 |
|---|---|---|---|
| POST EMERGENCE | | | |
| BUSH BEAN | 1B,2H | 1B | 0 |
| COTTON | 4B,4H | 1B | 1B,1H |
| MORNING GLORY | 2B,5H | 2G | 1B,2H |
| COCKLEBUR | 2G,6F | 0 | 0 |
| CASSIA | 5H | 2H | 0 |
| NUTSEDGE | 5G | 2G | 0 |
| CRABGRASS | 8G | 2H,7G | 5G |
| BARNYARD GRASS | 1B,8H | 7H | 5H |
| WILD OATS | 1B | 0 | 0 |
| WHEAT | 1B,6G | 0 | 0 |
| CORN | 1B,7H | 0 | 2E |
| SOYBEAN | 1B,4H | 1H | 0 |
| RICE | 1B,7G | 0 | 0 |
| SORGHUM | 1B,5G | 2G | 0 |
| PRE EMERGENCE | | | |
| MORNING GLORY | — | 0 | 5H |
| COCKLEBUR | 0 | 0 | 0 |
| CASSIA | 4H | 0 | 0 |
| NUTSEDGE | 10E | 2G | 10E |
| CRABGRASS | 9H 8H | 9H | |
| BARNYARD GRASS | 9H | 9H | 9H |
| WILD OATS | 9H | 2G | 8H |
| WHEAT | 9H | 8H | 9H |
| CORN | 9H | 8H | 9H |
| SOYBEAN | 4H | 0 | 2G |
| RICE | 9G | 8G | 9G |
| SORGHUM | 9H | 7H | 9H |

TABLE A-continued

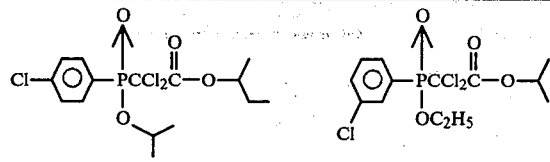

| kg/ha | 2 | 2/5 | 2 |
|---|---|---|---|
| POST EMERGENCE | | | |
| BUSH BEAN | — | — | 1B,3G |
| COTTON | — | — | 4B |
| MORNING GLORY | 1B,5H | 1H | 4G |
| COCKLEBUR | 0 | 0 | 4G |
| CASSIA | 1B,3H | 0 | 1B,8H |
| NUTSEDGE | 2G | 0 | 9G |
| GRABGRASS | 1B,8G | 3G | 1B,9G |
| BARNYARD GRASS | 1B,8H | 1H | 2B,9H |
| WILD OATS | 0 | 0 | 1B,9H |
| WHEAT | 0 | 0 | 1B,7H |
| CORN | 1B,2G | 0 | 1B,7H |
| SOYBEAN | 1H | 0 | 1B,5H |
| RICE | 4G | 0 | 1B,9G |
| SORGHUM | 1B | 0 | 1B,8H |
| PRE EMERGENCE | | | |
| MORNING GLORY | 0 | 0 | 3G |
| COCKLEBUR | — | — | 4G |
| CASSIA | 0 | 0 | 6H |
| NUTSEDGE | 0 | 0 | 10E |
| CRABGRASS | 4G | 0 | 10H |
| BARNYARD GRASS | 9H | 8H | 10H |
| WILD OATS | 2G | 0 | 9H |
| WHEAT | 9G | 7G | 9H |
| CORN | 7H | 1H | 9H |
| SOYBEAN | 0 | 0 | 4G |
| RICE | 5G | 2G | 10E |
| SORGHUM | 5G | 0 | 9H |

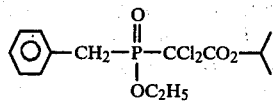

| kg/ha | 2 | 0.4 |
|---|---|---|
| POST EMERGENCE | | |
| BUSH BEAN | 1C,3H | 0 |
| COTTON | 4B | 1B,1H |
| MORNING GLORY | 1B | 1B,2H |
| COCKLEBUR | 1B | 0 |
| CASSIA | 1B,4H | 0 |
| NUTSEDGE | 8G | 0 |
| CRABGRASS | 8G | 5G |
| BARNYARD GRASS | 1B,7H | 5H |
| WILD OATS | 0 | 0 |
| WHEAT | 1B,4G | 0 |
| CORN | 1B,6H | 2G |
| SOYBEAN | 2H | 0 |
| RICE | 2G | 0 |
| SORGHUM | 1B,5G | 0 |
| PRE EMERGENCE | | |
| MORNING GLORY | 1C,7G | 5H |
| COCKLEBUR | 1H | 0 |
| CASSIA | 5H | 0 |
| NUTSEDGE | 10E | 10E |
| CRABGRASS | 10E | 9H |
| BARNYARD GRASS | 10H | 9H |
| WILD OATS | 9H | 8H |
| WHEAT | 9H | 9H |
| CORN | 9H | 9H |
| SOYBEAN | 6G | 2G |
| RICE | 10E | 9G |
| SORGHUM | 9H | 9H |

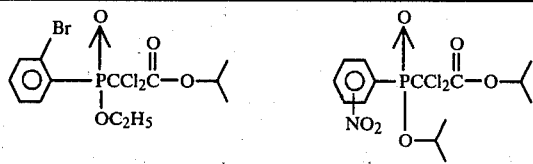

TABLE A-continued

| kg/ha | 2 | 2 | 2/5 |
|---|---|---|---|
| POST EMERGENCE | | | |
| BUSH BEAN | 1B,2H | 1B,6H | 4H |
| COTTON | 2B,2H | 5B | 1B,3H |
| MORNING GLORY | 1B | 2G | 3H |
| COCKLEBUR | 1B | 3G,6F | 1H |
| CASSIA | 2B | 1B,5H | — |
| NUTSEDGE | 5G | 7G | 6G |
| CRABGRASS | 1C,9G | 1C,8G | 7G |
| BARNYARD GRASS | 9H | 2C,9H | 1C,9H |
| WILD OATS | 0 | 1C,7G | 0 |
| WHEAT | 1C | 9G | 5G |
| CORN | 1C,6H | 9H/ 6H | |
| SOYBEAN | 1B,2H | 1B,5H | 3H |
| RICE | 1B,7G | 8G | |
| SORGHUM | 1B | 1B,7H | 4G |
| PRE EMERGENCE | | | |
| MORNING GLORY | 0 | 1C,7G | 2C,8G |
| COCKLEBUR | 0 | 2H | 2H |
| CASSIA | 0 | 5C,8G | 2C,6H |
| NUTSEDGE | 0 | 10E | 10E |
| CRABGRASS | 9H | 10H | 10H |
| BARNYARD GRASS | 9H | 10H | 10H |
| WILD OATS | 3G | 10H | 9H |
| WHEAT | 8G | 10H | 10H |
| CORN | 9H | 9H | 9H |
| SOYBEAN | 0 | 5C,9G | 6H |
| RICE | 4G | 10E | 10E |
| SORGHUM | 5G | 10H | 9H |

TEST B

Two plastic bulb pans were filled with fertilized and limed Fallsington silt loam soil. One pan was planted with corn, sorghum and several grassy weeds. The other pan was planted with soybeans, cotton, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), dallisgrass (*Paspalum dilatatum*), johnsongrass (*Sorghum halepense*), giant foxtail (*Setaria faberii*), Kentucky bluegrass (*Poa pratensis*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 5-inch diameter plastic pot was also filled with prepared soil and planted with rice and wheat. Another 5-inch pot was planted with sugarbeets. The above four containers were treated pre-emergence (compound sprayed on soil surface before seed germination).

Twenty eight days after treatment, the plants were evaluated, utilizing the rating system as described above for Test A. The data are summarized in Table B.

The results demonstrate that the compounds are useful for the selective control of weeds in a number of crops, including cotton, soybeans and sugarbeets.

TEST TABLE B

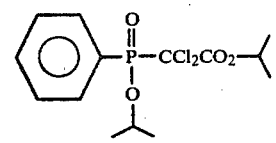

| Rate, kg/ha | 1 | 1/16 | ¼ | ½ | ⅛ |
|---|---|---|---|---|---|
| Crabgrass | 10E | 10H | 10E | 10E | 10E |
| Barnyardgrass | 10H | 9H | 10H | 10H | 10H |
| Sorghum | 10H | 6C | 5G, 3H | 7G, 5H | 10C |
| Wild oats | 10H | 20 | 8H | 9H | 10C |
| Johnsongrass | 10E | 8H | 10E | 10E | 10H |
| Dallisgrass | 10E | 9H | 10E | 10E | 10E |
| Giant foxtail | 10E | 10E | 10E | 10E | 10E |
| Ky. bluegrass | 10E | 10E | 10E | 10E | 10E |
| Cheatgrass | 10E | — | 6C | 9C | 10E |
| Sugarbeets | 7G | — | 3G | 6G | — |
| Corn | 9H | 0 | 7H | — | 8H |
| Mustard | 7C | — | 3G | 3G | — |
| Cocklebur | 2G | 0 | 0 | 0 | 0 |
| Pigweed | 10C | — | 4G | 3G | — |
| Nutsedge | 10E | 0 | 6G | 8G | 10E |
| Cotton | — | — | — | — | — |
| Morningglory | 10C | 0 | 5G | 4G | — |
| Cassia | 8G | — | 3G | 6G | — |
| Teaweed | 10C | — | 0 | 0 | — |
| Velvetleaf | 10C | — | 3G | 5G | — |
| Jimsonweed | 10C | — | 0 | 6G | — |
| Soybean | 10C | 0 | 4G | 4G | 6G, 3H |

TEST TABLE B-continued

| | | | | | | | |
|---|---|---|---|---|---|---|---|
| Rice | 10C | 0 | 8G | | 8G | | 8H |
| Wheat | 8G, 8C | 0 | 7G | | 8G | | 7G |

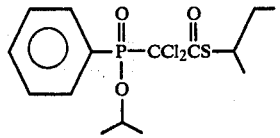

| Rate, kg/ha | ⅛ | ⅛ | ⅛ | ⅛ | 1/16 | ⅛ | ⅛ |
|---|---|---|---|---|---|---|---|
| Crabgrass | 4H | 8H | 9H | 10H | 10C | 10C | 10C |
| Barnyardgrass | 2H | 8H | 9H | 10E | 9H | 8H | 9H |
| Sorghum | 0 | 0 | 3H | 10H | 3H | 3H | 10H |
| Wild oats | 0 | 0 | 2H | 7H | 0 | 0 | 4H |
| Johnsongrass | 0 | 5H | 7H | 10H | 6H | 8H | 10H |
| Dallisgrass | 0 | 5H | 8H | 9H | 8H | 10H | 10H |
| Giant foxtail | 0 | 7H | 5H | 9H | 10C | 10C | 10C |
| Ky. bluegrass | 3H | 7H | 9H | 9H | 9H | 7H | 10H |
| Cheatgrass | 0 | 3H | 0 | 10H | 4C | 4C | 9C |
| Sugarbeets | 0 | 0 | 0 | 0 | — | — | — |
| Corn | 0 | 0 | 5H | 8H | 2H | 4H | 6H |
| Mustard | 0 | 0 | 0 | 6G, 3C | 3G | 3G | 8C |
| Cocklebur | 0 | 0 | 0 | 4G | 0 | 0 | 0 |
| Pigweed | 0 | 0 | 10C | 10C | 0 | 5C | 9C |
| Nutsedge | 0 | 3G | 3G | 9G | 0 | 0 | 6C |
| Cotton | 0 | 0 | — | — | — | — | — |
| Morningglory | 0 | 0 | 0 | 4C | 0 | 0 | 8C |
| Cassia | — | — | 0 | 5C | — | — | — |
| Teaweed | 0 | 0 | 0 | 9C | 0 | 0 | — |
| Velvetleaf | 0 | 0 | 0 | 5C | — | — | — |
| Jimsonweed | 0 | 0 | 0 | 9C | 0 | 0 | 3G |
| Soybean | 0 | 0 | 4H | 8H | 0 | 0 | — |
| Rice | 0 | 3G | 6H | 4H | 0 | 3G | 8G |
| Wheat | 0 | 4G | 2H | 9H | 0 | 2G | 3G |

TEST C

Seeds of the crops and weeds listed in table C were planted in plastic pots filled with Fallsington silt loam. Each pot contained a number of corn, soybean and cotton seeds at a planting depth of 2.5 cm. The layer of soil above the crop seeds was uniformly infested with seeds of the following weed species: crabgrass (*Digitaria spp.*), barnyardgrass (*Echinochloa crusgalli*), giant foxtail (*Setaria faberii*), and johnsongrass (*Sorghum halepense*). Promptly after planting, the test chemical was applied to the surface of the soil, dissolved in a non-phytotoxic solvent. The treated pots were then exposed to approximately 4 mm of simulated rainfall and transferred to the greenhouse. Twenty-eight days after treatment, the estimated percentages of grass weed control were recorded and observations were made on crop response, again utilizing the rating system as described for test A. The data are shown in table C. It is obvious that the test compound possesses utility for the pre-emergence control of grass weeds in soybeans and cotton.

TABLE C

| Chemical Structure | Rate (kg/ha) | % Control grass weeds | Corn | Soy-beans | Cotton |
|---|---|---|---|---|---|
| 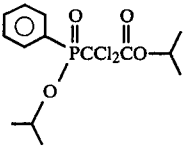 | 1/64 | 50 | 0 | 0 | 0 |
| | 1/32 | 85 | 4G | 0 | 0 |
| | 1/16 | 98 | 7H | 0 | 0 |
| | ⅛ | 100 | 7H | 0 | 0 |
| | ⅛ | 100 | 7H | 0 | 2G |

TABLE C-continued

| Chemical Structure | Rate (kg/ha) | % Control grass weeds | Corn | Soy-beans | Cotton |
|---|---|---|---|---|---|
| Untr. Control | — | 0 | 0 | 0 | 0 |

TEST D

Plastic bulb pans containing fertilized Fallsington silt loam were planted to corn, soybeans and cotton, planting depth 2.5 cm. The covering 2.5 cm layer of soil had been uniformly infested with a mixture of seeds of the following weed species: crabgrass (*Digitaria sanguinalis*), barnyardgrass (*Echinochloa crusgalli*), giant foxtail (*Setaria faberii*), johnsongrass (*Sorghum halepense*), velvetleaf (*Abutilon theophrasti*), jimsonweed (*Datura stramonium*), and mustard (*Brassica arvensis*). Immediately after planting, the soil surfaces were treated with a solution in a non-phytotoxic solvent of the compound whose structure is shown in Table D. One group of pots served as pre-emergency treatments; a second group was used to simulate soil-incorporated treatments whereby the surface-applied chemical was promptly mixed with the top 2.5 cm layer of soil containing the weed seeds. All of the pots were then watered from overhead at the rate of approximately 4 mm of water in a period of 160 minutes. The treated pots and controls were held in a greenhouse and on the twenty-eighth day after treatment were visually rated using the same scale and symbols as described herein before. The data are shown in Table D.

TABLE D

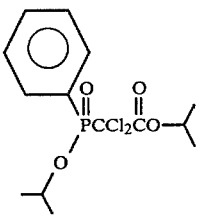

| Rate kg/ha | 1/32 | 1/16 | 1/8 | 1/4 | 1 |
|---|---|---|---|---|---|
| PRE-EMERGENCE | | | | | |
| Weeds | | | | | |
| Broadleaves | 0 | 0 | 0 | 2C | 8C |
| Grasses | 4H | 7H | 9H | 10H | 10H |
| Crops | | | | | |
| Corn | 0 | 0 | 0 | 5G | 9H |
| Soybeans | 0 | 0 | 0 | 0 | 2H |
| Cotton* | — | 0 | — | 0 | 0 |
| INCORPORATED | | | | | |
| Weeds | | | | | |
| Broadleaves | 0 | 0 | 2C | 2C | 9C |
| Grasses | 4H | 8H | 9H | 10H | 10H |
| Crops | | | | | |
| Corn | 0 | 0 | 0 | 7H | 10H |
| Soybeans | 0 | 0 | 0 | 3G | 8H |
| Cotton* | 3G | 0 | 3G | 3G | 3G |

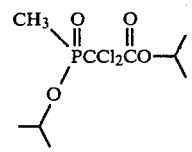

| Rate kg/ha | 1/32 | 1/16 | 1/8 | 1/4 | 1 |
|---|---|---|---|---|---|
| PRE-EMERGENCE | | | | | |
| Weeds | | | | | |
| Broadleaves | 0 | 0 | 0 | 3C | 4C |
| Grasses | 0 | 0 | 0 | 2H | 7H |
| Crops | | | | | |
| Corn | 0 | 0 | 0 | 0 | 0 |
| Soybeans | 0 | 0 | 0 | 0 | 0 |
| Cotton* | 0 | 0 | 0 | 0 | 3G |
| INCORPORATED | | | | | |
| Weeds | | | | | |
| Broadleaves | 0 | 0 | 0 | 0 | 3C |
| Grasses | 0 | 0 | 0 | 2H | 7H |
| Crops | | | | | |
| Corn | 0 | 0 | 0 | 0 | 10H |
| Soybeans | 0 | 0 | 0 | 0 | 2G |
| Cotton* | 0 | 0 | 0 | 0 | 2G |

*Poor Stands

What is claimed is:

1. A compound of the formula:

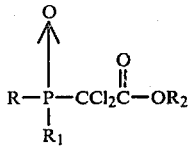

wherein
R is $C_1$–$C_4$ alkyl or phenyl;
$R_1$ is $C_1$–$C_4$ alkoxy or $NR_{11}R_{12}$;
$R_2$ is alkyl of 1–6 carbons, alkenyl of 3–4 carbons, cycloalkyl of 5–6 carbons or said cycloalkyl substituted with one methyl; and
$R_{11}$ and $R_{12}$ are independently H or $C_1$–$C_4$ alkyl.

2. A compound of claim 1 wherein $R_2$ is $C_1$–$C_4$ alkyl.

3. The compound of claim 1, 1-methylethyl 2,2-dichloro[(1-methylethoxy)phenylphosphinyl]acetate.

4. The compound of claim 1, 1-methylpropyl 2,2-dichloro-2-[(1-methylethoxy)phenylphosphinyl]acetate.

5. The compound of claim 1, 1-methylethyl 2,2-dichloro-2-[(n-butoxy)phenylphosphinyl]acetate.

6. The compound of claim 1, 1-methylethyl 2,2-dichloro-2-[(1-methylethoxy)methylphosphinyl]acetate.

7. The compound of claim 1, 1-methylethyl 2,2-dichloro-2-[(ethoxy)methylphosphinyl]acetate.

8. The compound of claim 1, 1-methylethyl 2,2-dichloro-2-[(n-propoxy)phenylphosphinyl]acetate.

9. The compound of claim 1, 1-methylethyl 2,2-dichloro-2-[(ethoxy)ethylphosphinyl]acetate.

* * * * *